US012635875B2

(12) United States Patent
Alasirnio et al.

(10) Patent No.: US 12,635,875 B2
(45) Date of Patent: May 26, 2026

(54) APPARATUS AND METHOD FOR OPHTHALMIC IMAGING

(71) Applicant: OIVI AS, Oslo (NO)

(72) Inventors: Jukka Alasirnio, Jaali (FI); Hans Einar Overjordet, Asker (NO); Anders Eikenes, Jar (NO)

(73) Assignee: Oivi AS, Oslo (NO)

( * ) Notice: Subject to any disclaimer, the term of this patent is extended or adjusted under 35 U.S.C. 154(b) by 556 days.

(21) Appl. No.: 18/042,246

(22) PCT Filed: Aug. 20, 2021

(86) PCT No.: PCT/GB2021/052168
§ 371 (c)(1),
(2) Date: Feb. 20, 2023

(87) PCT Pub. No.: WO2022/038373
PCT Pub. Date: Feb. 24, 2022

(65) Prior Publication Data
US 2024/0008740 A1      Jan. 11, 2024

(30) Foreign Application Priority Data

Aug. 21, 2020      (GB) ..................................... 2013062

(51) Int. Cl.
| | |
|---|---|
| *A61B 3/00* | (2006.01) |
| *A61B 3/12* | (2006.01) |
| *A61B 3/14* | (2006.01) |

(52) U.S. Cl.
CPC .............. *A61B 3/12* (2013.01); *A61B 3/0008* (2013.01); *A61B 3/14* (2013.01)

(58) Field of Classification Search
CPC .......... A61B 3/12; A61B 3/0008; A61B 3/14; A61B 3/0083; A61B 3/1208
See application file for complete search history.

(56) References Cited

U.S. PATENT DOCUMENTS

| | | | | |
|---|---|---|---|---|
| 5,120,122 A | * | 6/1992 | McAdams | A61B 3/14 351/211 |
| 7,670,002 B2 | * | 3/2010 | Stark | A61B 3/112 351/205 |
| 10,588,781 B2 | * | 3/2020 | Kim | A61F 9/00821 |
| 11,504,000 B2 | * | 11/2022 | Khan | A61B 3/0008 |
| 2003/0208125 A1 | * | 11/2003 | Watkins | A61B 3/12 600/476 |
| 2006/0171275 A1 | * | 8/2006 | Nishikawa | G11B 19/128 369/53.2 |
| 2009/0195750 A1 | * | 8/2009 | Isogai | A61B 3/0083 351/208 |

(Continued)

*Primary Examiner* — Balram T Parbadia
*Assistant Examiner* — John Curtis Sipes
(74) *Attorney, Agent, or Firm* — Kevin J Fournier Intellectual Property Legal Services Ltd.; Kevin J Fournier

(57) ABSTRACT

A portable ophthalmic imaging device suitable for imaging an eye having a first optical axis is provided. The imaging device comprises an imaging module comprising a plurality of optical elements including a light sensor which define a second optical axis; an eye rest; and a plurality of motors. The plurality of motors are arranged to move the imaging module and/or the eye rest to align the first and second optical axes at least partially automatically using a feedback control system.

16 Claims, 16 Drawing Sheets

(56)            References Cited

U.S. PATENT DOCUMENTS

| | | | | |
|---|---|---|---|---|
| 2009/0303600 | A1* | 12/2009 | Matsumoto | G02B 27/4216 |
| | | | | 359/796 |
| 2015/0351623 | A1* | 12/2015 | Watanabe | A61B 3/152 |
| | | | | 351/246 |
| 2016/0073876 | A1* | 3/2016 | Akita | G02B 27/145 |
| | | | | 351/206 |
| 2016/0183788 | A1* | 6/2016 | Abramoff | A61B 3/0008 |
| | | | | 351/208 |
| 2018/0055358 | A1* | 3/2018 | Nakajima | A61B 3/15 |
| 2019/0110753 | A1* | 4/2019 | Zhang | G06N 3/084 |
| 2019/0269323 | A1* | 9/2019 | Cornsweet | A61B 3/0091 |
| 2020/0129062 | A1* | 4/2020 | Glik | A61B 3/0091 |
| 2020/0323427 | A1* | 10/2020 | Gharib | A61B 3/1241 |
| 2020/0367746 | A1* | 11/2020 | Miller | A61F 9/008 |
| 2021/0315455 | A1* | 10/2021 | Delong | A61B 3/14 |
| 2022/0211267 | A1* | 7/2022 | Leung | A61B 3/12 |
| 2022/0257114 | A1* | 8/2022 | Schottner | A61B 3/12 |
| 2022/0283327 | A1* | 9/2022 | Mueller | G01C 11/06 |

* cited by examiner

1

APPARATUS AND METHOD FOR OPHTHALMIC IMAGING

The present invention relates to imaging of the eye, particularly to diagnose health problems.

Vision loss is a global issue, with many conditions which cause vision loss treatable but undiagnosed, leading to further vision degeneration and blindness. Vision loss is associated with adverse social and financial consequences, particularly in developing nations where access to preventative healthcare and treatment can be difficult due to lack of specialist facilities and transport links.

The fundus of the eye is the interior lining of the eyeball, including the retina, optic disc and macula. Imaging of the fundus of the eye can be used for screening and monitoring of eye conditions and diseases including diabetes, age-related macular degeneration and glaucoma. Regular screenings, particularly in patients with diabetes can be important to screen for diabetic retinopathy which can be prevented with treatment if spotted early and therefore prevent long term vision loss.

Imaging of the fundus of the eye is normally carried out by trained professionals, who are able to perform this in the best way to ensure optimal imaging. However, there is a lack of trained professionals who are able to carry out this work, particularly in rural areas and developing countries. In addition, conventional ophthalmic imaging devices are large and complex, requiring a specialist setting where they can be installed, operated and maintained. For many people however, access to these services is very difficult if they live in remote areas.

According to a first aspect of the present invention there is provided a portable ophthalmic imaging device suitable for imaging an eye having a first optical axis, the imaging device comprising:

an imaging module comprising a plurality of optical elements including a light sensor which define a second optical axis;

an eye rest; and a plurality of motors, wherein the plurality of motors are arranged to move the imaging module and/or the eye rest to align the first and second optical axes at least partially automatically using a feedback control system.

Thus it will be seen by those skilled in the art that in accordance with the invention, an imaging device can at least partially automatically align the second optical axis of the imaging module with the first optical axis of the patient's eye which is being imaged using the motors to move the imaging module and/or eye rest. The second optical axis typically extends through the geometric centre of the imaging module, parallel to the linear extent of the imaging module. There is no need for a trained person to carry out the imaging as the device itself can automatically adjust the position of the internal imaging module and/or the eye rest for alignment between the first optical axis of the patient's eye and the second optical axis of the imaging module. This means that at least in some embodiments of the invention, high quality, accurate images can be achieved with no training required for the person performing the imaging. The alignment process may be triggered manually—e.g. by the person carrying out the imaging pressing a button, or automatically—e.g. when the device is picked up or detects that it is close to an eye, alignment could require no input from the user or the user could carry out an initial, crude alignment.

The automatic alignment may be achieved in a number of ways. In a set of embodiments the feedback control system comprises a processor and is arranged to capture an initial image with no adjustment of the imaging module and/or eye rest. Such an image may be analysed for brightness and/or contrast and/or sharpness, or compared to an ideal sample image and the motors used to adjust the position of the imaging module and/or eye rest in order to improve the image, for example by improving the contrast and/or sharpness of the image. This process may be repeated until an optimised image is captured by the imaging device. In a set of embodiments an algorithm based on machine learning trained using adjustments undertaken by skilled practitioners may be used to align the first and second optical axes by controlling the motors arranged to move the imaging module and/or eye rest.

In a set of embodiments the imaging module itself is used for alignment. However the Applicant has recognised that this would require the main imaging module to be designed with a wide enough field of view to provide a view of the pupil whilst being aligned to the retina. In some circumstances if the imaging module is too close to detect the pupil and/or retina then the captured image cannot contain enough information for alignment to start. In this case, as the iris and fundus would be imaged with the same sensor, the system would require additional optical elements to avoid direct and indirect reflections and scattering of light from the light source to the sensor in order to maintain the signal to noise ratio of the system. If the same sensor is used to image both the iris for alignment and the fundus, the imaging module may be moved from a position further from the eye, when the iris would be visible allowing alignment of the imaging system to the pupil, to a position closer to the eye, where only the fundus would be visible. Such a system may be prone to errors as it would require the patient to keep the eye completely still during the alignment procedure.

In a set of preferred embodiments therefore, the imaging device further comprises an alignment sensor e.g. mounted on an exterior portion of the imaging device. Such an alignment sensor may be used to detect the pupil of the eye in order to determine its location and gaze direction and thus the first optical axis. This information may then be used by the processor to determine the necessary motor movements for alignment without needing to use the imaging module (although this could also be used in addition if desired). The alignment sensor could be non-optical e.g. using ultrasound or infra-red sensors, but in a set of embodiments the alignment sensor comprises an alignment camera arranged to determine alignment optically. In a set of embodiments two separate alignment sensors (e.g. cameras) are provided. In such a case a more accurate 3D positioning of the pupil relative to the imaging module may be calculated through use of stereo imaging.

Use of a dedicated alignment camera or other sensor to image the pupil for alignment means that the main optics and sensor of the imaging module can be designed and optimised to capture only images of the fundus of the eye. It may also reduce the required complexity and range of movement of the motors and associated mechanisms. Using an alignment camera may also ensure a more robust alignment of the first and second optical axes.

As the ophthalmic imaging device is portable, it can therefore be used in remote locations without a need for a specialist laboratory or clinic location. Embodiments of the invention can be used in a multitude of ways, such as being handheld, placed on a horizontal surface such as a table, or mounted on a wall/ceiling. Embodiments may allow imaging to be carried out by a skilled person, non-skilled person or the patient. High quality images may still be captured with no specific training in aligning the device correctly. The imaging device could be either be designed so that in use it is moved towards the patient by the person carrying out the imaging, or the patient themselves, or instead so that the patient can move themselves towards the imaging device.

The plurality of optical elements preferably includes one or more lenses arranged to image the fundus of the eye onto a sensor, with subsequent image analysis. The eye rest is typically arranged to enable the patient to place the eye rest against the orbital of their skull (the socket of the skull in which the eye is situated) to provide a fixed point against which the imaging device can be used to take images.

In a set of embodiments, the portable imaging device is battery powered. This may avoid limitations to having to use the imaging device only in locations where a wired power connection is available. In a set of such embodiments, the battery powered imaging device is rechargeable through docking with a base unit to form a temporary wired connection. For example, the base unit may comprise a first set of electrical contacts and the imaging device may comprise a second set of electrical contacts to be brought into contact with the first set of electrical contacts to form the temporary wired connection. In some embodiments the electrical contacts can be replaced by inductive charging (such as the Qi contactless charging standard). In some embodiments, the imaging device and base unit may be arranged to form a wired connection using a cable (e.g. a USB cable). This wired or alternatively wireless connection may provide power from the base unit to the battery powered imaging device in order to recharge the batteries of the imaging device. In another set of embodiments, the batteries can be removed from the imaging device and replaced when they no longer provide sufficient power.

In a set of embodiments, a temporary wired connection or a wireless connection may be used to transfer data from the imaging device to a or the base unit. For example, the imaging device may be arranged to transfer stored images from an associated memory portion to the base unit over the temporary wired connection or wireless connection.

In a set of embodiments, the imaging device includes a removable data storage device, such as a flash memory card. In some such embodiments the base unit (where provided) may comprise a corresponding data storage device reader (e.g. a memory card slot), allowing a user to transfer the stored data (such as optimised images of the fundus of the eye) from the imaging device to the base unit by removing the removable storage device from the imaging device and providing it to the storage device reader (e.g. by inserting it into a memory card slot).

In a set of embodiments, the base unit can communicate with an external system over a wireless link (e.g. over a Radio Frequency (RF) connection such as a connection conforming to the Bluetooth™ or WiFi standards). The base unit may be arranged to transmit stored image data from the imaging device which has been connected to the base unit via a temporary wired connection to the external system or from the removable storage device. In another set of embodiments the imaging device is arranged to communicate directly with the external system via a wireless connection. Either way the external system may thus receive images of the fundus of the patient's eye which can be reviewed by specialists at another location. The images which have been captured by the imaging device may therefore be used to inform treatment or further referrals, which may not have otherwise been possible for patients who were unable to access a specialist medical facility but can now be identified as requiring treatment.

In a set of embodiments the imaging device comprises a processor arrangement programmed to perform an artificial intelligence algorithm that analyses captured images and provides information regarding whether a further referral is necessary. Such information could be displayed on the imaging device e.g. on a display provided thereon. The same information may also or instead be provided to an external system via the wireless or wired connection. The processor arrangement could include the processor previously described or the imaging device could comprise a separate AI processor.

In a set of embodiments, the plurality of motors are arranged to move the imaging module which houses the internal optics to manipulate the position of the internal optics relative to the patient's eye and provide alignment between the first optical axis of the eye which is being imaged and the second optical axis of the imaging module. These motors may be used to provide any or all of the six dimensions of movement (XYZ, pan, tilt and roll) of the imaging module to facilitate alignment. In addition, a focus motor may be provided to compensate for the eye's refractive error (near- or far-sightedness). Each motor may be arranged to move the imaging module through independently pushing or pulling the part of the imaging module to which it is connected in order to facilitate alignment.

In a set of embodiments, one or more motors are arranged to move the eye rest and one or more motors are arranged to move the imaging module, such that the eye rest can be moved independently from the imaging module. In one example, the eye rest position may be changed in the XYZ direction and the imaging module orientation may be independently controlled in the pan and tilt directions by the respective motors. The combination of the independent movements of the eye rest and imaging module may enable a wider range of relative movement between the eye being imaged and the imaging device and internal optics than if motors are only arranged to move the eye rest or only arranged to move the imaging module. This wider range of movement may enable the imaging device to more easily and accurately align the second optical axis of the internal imaging module with the first optical axis of the patient's eye.

In a set of embodiments the imaging module is fixed to a swivel point about which it can be rotated by its associated motors to align the imaging module with the eye being imaged. The position of the swivel point may be selected to be any point along the length of the imaging module.

In a set of embodiments the plurality of motors are symmetrically arranged around the second optical axis of the imaging module. For example, three motors may be distributed evenly at angular separations of 120° around the imaging module and arranged to move the imaging module. Each motor may be arranged such that it can either independently pull or push the imaging module as is required for alignment with the patient's eye.

In a set of embodiments, the plurality of motors are asymmetrically arranged around the second optical axis of the imaging module. For example, only two motors may be used, at an angular separation of 90°. Again, the motors may be arranged to move the imaging module, with each motor arranged such that it can either push or pull the imaging module.

In a set of embodiments, the plurality of motors are distributed along the length of the imaging module, for example with two motors at one end of the imaging module, and two motors at the opposite end of the imaging module.

In a set of embodiments, the imaging module is fixed to a Stewart platform for manipulation of the position of the optical arrangement. The imaging module can either be fixed to the top of the platform horizontally and parallel to the platform, or through the centre point (the geometric centre) of the platform and perpendicular to the platform. The Stewart platform may allow for movement of the imaging module in any of the six degrees of freedom (XYZ, pan, tilt and roll) through adjustment of the platform using motors.

In order that sufficient motion for alignment can be achieved by the imaging module and/or the eye rest, it is necessary to have a plurality of motors. Having fewer motors connected to the imaging module and/or eye rest may increase the mechanical complexity of the imaging device, as to achieve the necessary movements for alignment of the first and second optical axes, more linkages, pivots etc. may be needed to compensate for the reduced number of motors. On the other hand, having more motors connected to the imaging module and/or eye rest may reduce the mechanical complexity of the imaging device. However, a higher total number of motors will increase the weight and size of the imaging device. Therefore, depending on where the imaging device will be used, the number of motors connected to the imaging module and/or eye rest may be optimised according to the acceptable mechanical complexity, size and weight for the imaging device in that situation.

The device could be arranged to engage with one eye at a time so that in order to image both eyes, the device must be repositioned. In another set of embodiments the motors and their operating/travel length are selected so that both eyes of the patient can be imaged without the need to reposition the device.

The Applicant has further appreciated that when capturing an image of the fundus of the eye, high light intensity leads to a high signal to noise ratio on the captured picture. However, using high intensity visible light causes contraction of the pupil, reducing the light entering the eye as well as making image capture more difficult due to the reduced pupil size.

In a set of embodiments the imaging device further comprises one or more light sources arranged to illuminate the eye at at least two different wavelengths;

the feedback control system being arranged to use light at a first wavelength for aligning said first and second optical axes; and the imaging module being arranged to image the eye at a second wavelength when the first and second optical axes are aligned.

The light used for alignment may be chosen to be at one or more wavelengths that do not cause the pupil to contract, meaning that high intensity visible light needs only to be used to capture an image when alignment and optionally focus, has been achieved. This allows high intensity visible light to be used to illuminate the eye for a short time such that pupil contraction will be minimal.

Such an arrangement is novel and inventive in its own right and thus when viewed from a further aspect, the present invention provides a portable ophthalmic imaging device suitable for imaging an eye, the imaging device comprising:

one or more light sources arranged to illuminate the eye at at least two different wavelengths;

a camera; and an alignment system;

wherein the imaging device is arranged to illuminate the eye at a first wavelength while aligning the eye and the camera using the alignment system, and to illuminate the eye at a second wavelength while imaging the eye using the camera.

In a set of embodiments of either aspect of the invention the imaging device further comprises a focusing system arranged to focus the imaging module automatically on the patient's fundus. In a set of such embodiments the one or more light sources is/are also arranged to illuminate the eye during focusing. This could be carried out at the first wavelength or a third, different, wavelength.

In a set of embodiments of either aspect of the invention, the camera or imaging module includes one or more achromatic lenses. When the camera or imaging module is used for alignment and/or focusing and imaging, the use of an achromatic lens configuration may ensure that the focal length during alignment and/or focusing using light at the first (and optionally third) wavelength will also be the correct focal length for the image taken using light at the second wavelength. This will ensure that a refocusing is not required when shifting between the first (, third) and second wavelengths, hence speeding up the image capture procedure, and/or not requiring the patient to keep still during alignment and/or focusing and image capture.

In an alternative set of embodiments of either aspect of the invention, the imaging device further comprises an alignment camera e.g. mounted on an exterior portion of the imaging device. The alignment camera may image the eye using light at the first wavelength, with the alignment system using these images for alignment of the optical axes of the imaging device and eye. The optional focusing system (e.g. within the imaging module) may then focus the image to create a sharp image using light at the first or third wavelength. Then the imaging module or camera may image the eye using light at the second wavelength. As previously explained, use of a dedicated alignment camera to image the pupil for alignment means that the imaging module or camera can be designed and optimised to capture only images of the fundus of the eye. The full resolution of the imaging module or camera can therefore be used for the final image.

A common light source could be used to produce both or all three wavelengths (where employed) but in a set of embodiments of either aspect of the invention, the light sources for the respective wavelengths are separate. For example, where provided, the alignment camera may have one light source to illuminate the eye at the first wavelength and the imaging module or camera may have another, separate light source to illuminate the eye at the second wavelength. However separate light sources could also be used where the imaging module or camera is used for alignment and/or focusing and imaging.

In a set of embodiments of either aspect of the invention, light at the first (and optionally third) wavelength is infra-red (IR) light and light at the second wavelength is visible light. The visible light may be white light, or red, green and blue used to produce RGB images, or it may be a single wavelength or other combination of wavelengths. It is also possible to capture several narrow wavelength pictures, for example several infrared and single visible wavelength pictures for more detailed analysis of eye condition(s) compared to previously described methods for visible imaging.

In a set of embodiments, there is a reticle or other type of focus target inside the imaging module, which is visible to the patient. There might also be one or multiple LED's which the patient is asked to gaze at, providing a fixation target, to make sure the eye is kept relatively still during alignment and image capture.

In another embodiment an external light source can illuminate the reticle or other focus target making it visible for the patient during alignment, but briefly shutting it off while capturing the RGB image to improve image quality.

Features of any aspect or embodiment described herein may, wherever appropriate, be applied to any other aspect or embodiment described herein. Where reference is made to different embodiments, it should be understood that these are not necessarily distinct but may overlap.

One or more non-limiting examples will now be described, by way of example only, and with reference to the accompanying figures in which.

Figure 1A:
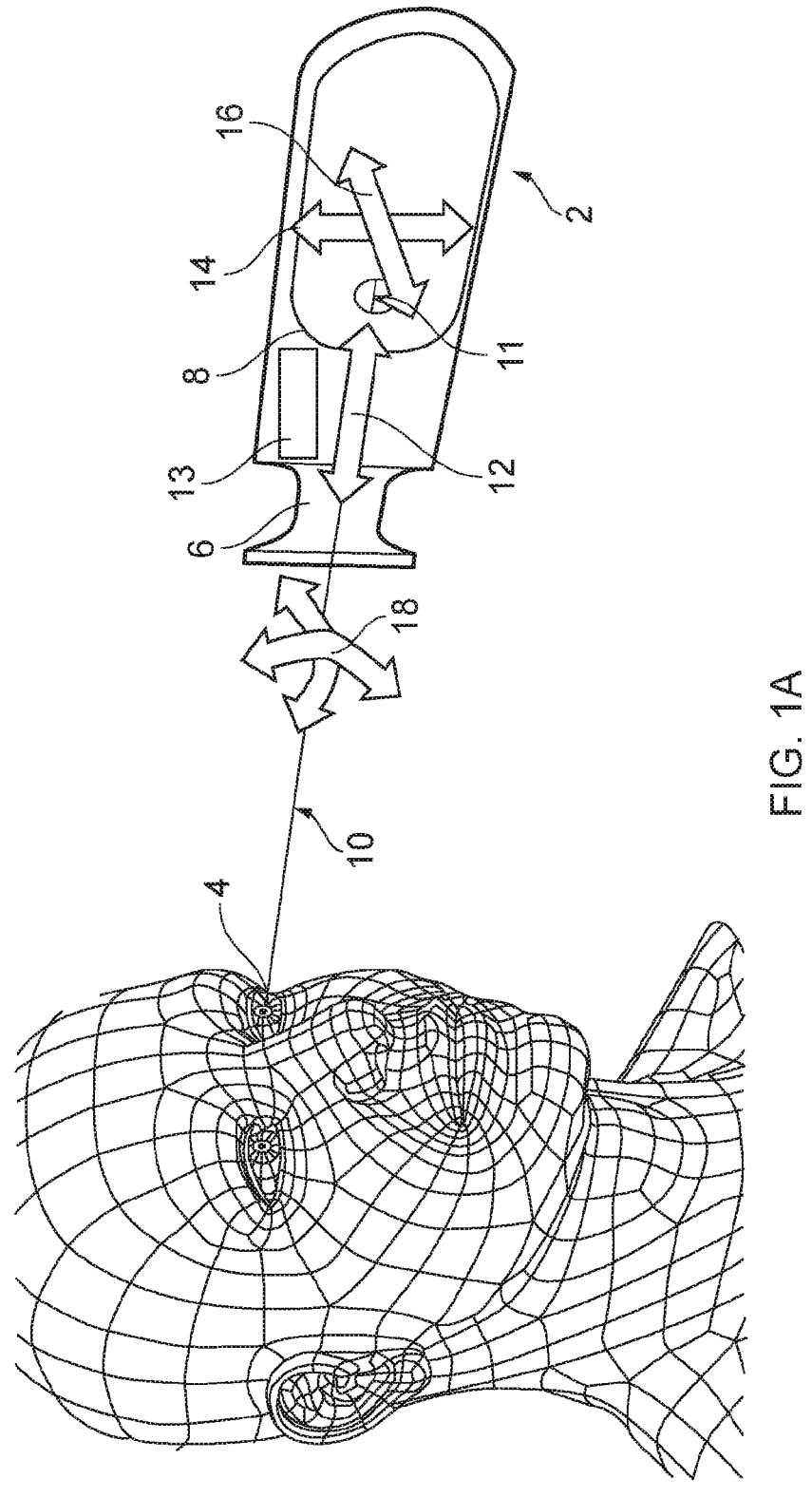
FIG. 1A is a schematic diagram of an imaging device in accordance with the invention used to image the fundus of an eye.

FIG. 1A is a schematic diagram of an imaging device 2 being used to image the fundus of a patient's eye 4. The imaging device comprises an eye rest 6, imaging module 8 and associated motors (see FIG. 2). The first optical axis is defined by a line extending from the centre of the macula through the centre of the pupil of the patient's eye 4 to be imaged. The second optical axis 11 is an axis around which there is rotational symmetry in the imaging module 8. For optimal imaging, the first and second optical axes need to be aligned. The display screen 13 is visible to the user on the imaging device 2.

Figure 1B:
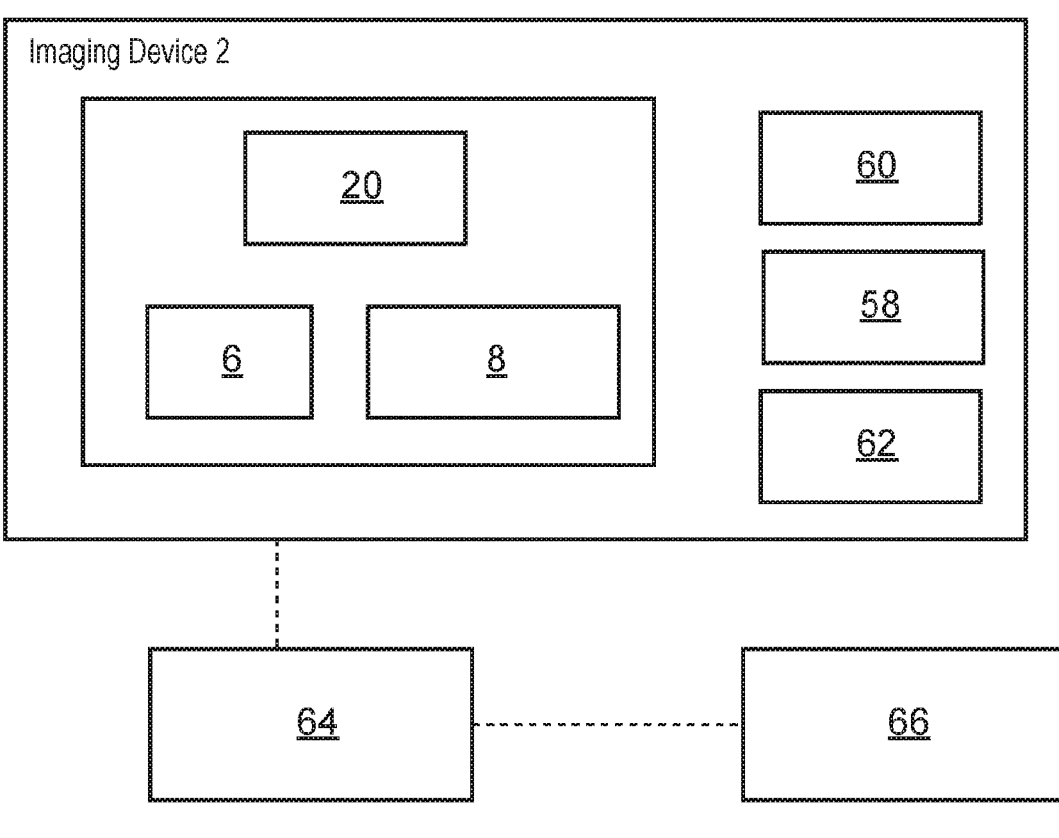
FIG. 1B is a schematic diagram of an imaging system using the imaging device of FIG. 1A.

FIG. 1B is a schematic diagram of an imaging system which includes the imaging device 2 which further comprises a battery 58, processor 60 and memory 62. The imaging device 2 may have a wired or wireless connection to a base unit 64. The base unit 64 communicates with an external server 66. Alternatively the imaging device 2 can communicate directly with the external server 66. It is also possible that a personal computer or tablet can act as the base unit 64 and/or external server 66.

The automated alignment of the first 10 and second 11 optical axes may be achieved using a feedback control system which comprises the processor The processor 60 may also be programmed to perform an artificial intelligence algorithm that analyses captured images and provides information on the display screen 13 which outputs the result of this local AI analysis on the captured image. Alternatively the device 2 may comprise a separate AI processor.

The base unit 64 may be used to charge the imaging device 2 via the wired or wireless connection. The base unit 64 may also be programmed to perform an AI algorithm which analyses the captured images on the imaging device 2, and may also display the results or other relevant information such as image reliability analysis or similar on its screen.

Figure 2:
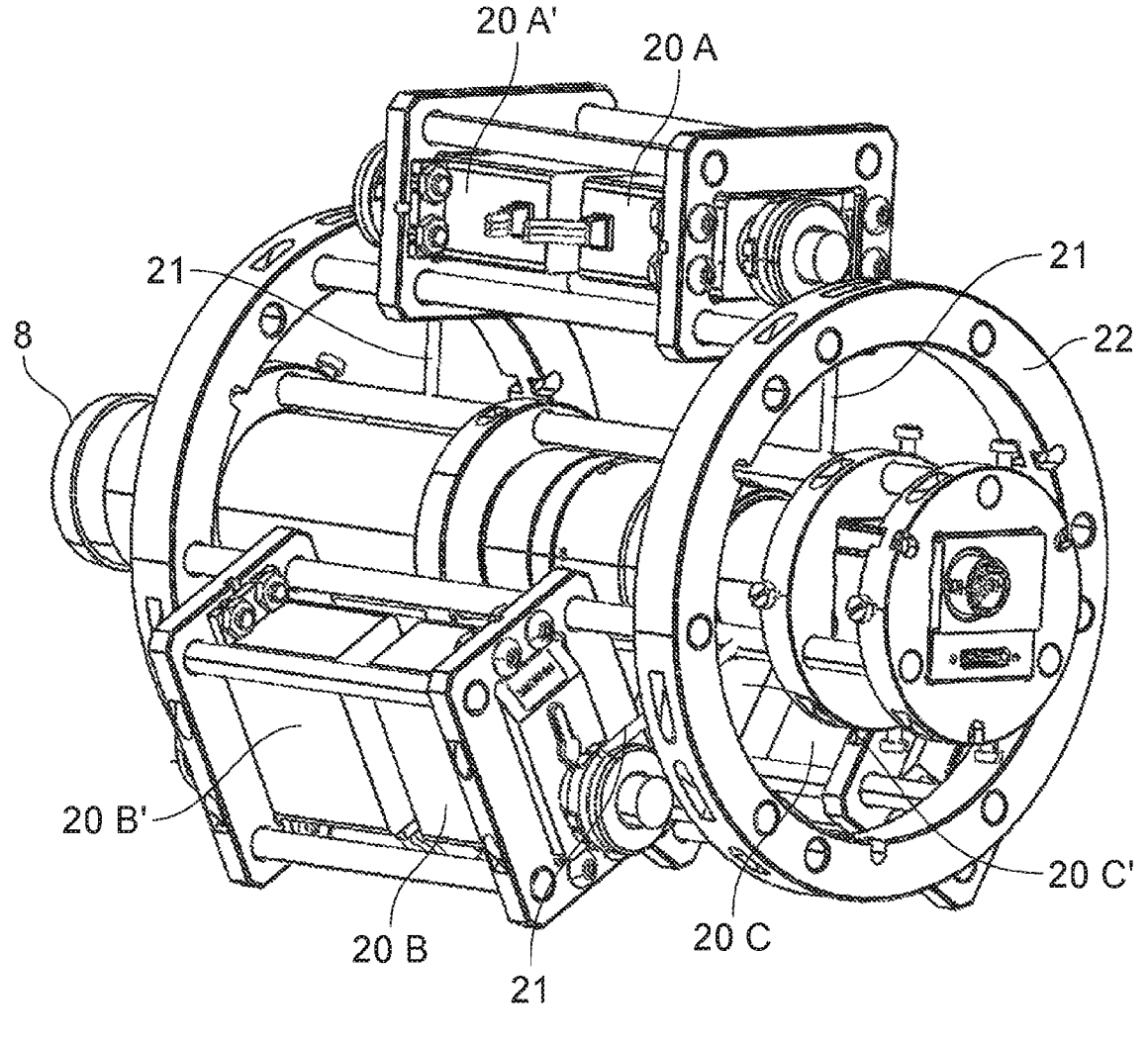
FIG. 2 shows the external motor configuration surrounding the imaging module in the embodiment of FIG. 1A.

FIG. 2 shows the external motor configuration surrounding the imaging module 8 from FIG. 1A. The motors 20 A, B and C are spaced equidistantly around the imaging module 8 at the same position along the length of the imaging module 8. The motors 20 A', B' and C' are also spaced equidistantly around the imaging module 8 at the same position along the length of the imaging module 8, at the opposite end of the imaging module 8 to the motors 20 A, B, C. The motors 20 are connected to a support structure 22 and to the imaging module 8 via connections 21. The connections 21 may be threads which can only pull on the imaging module 8, not push. A specific five-axis position of the imaging module 8 would be dictated by a specific configuration of the six motors with specific lengths of the threads (connections 21).

Figure 3A:
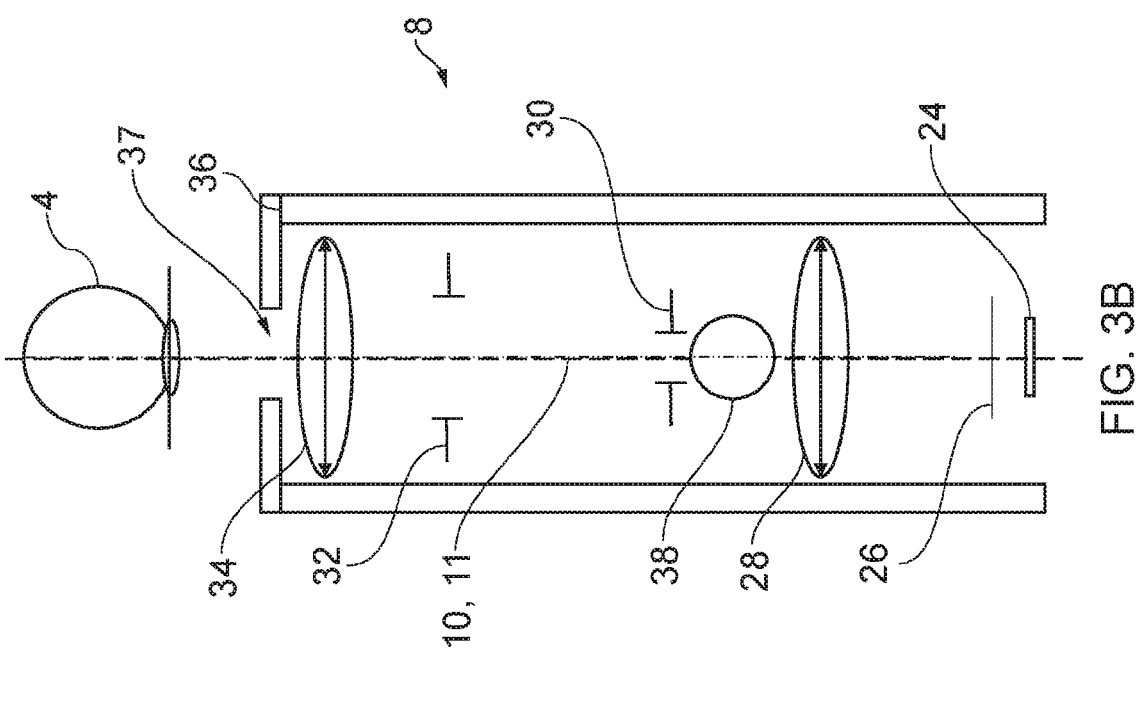
FIG. 3A is a schematic diagram of the optical elements contained within the imaging module prior to alignment of the first and second optical axes.
Figure 3B:
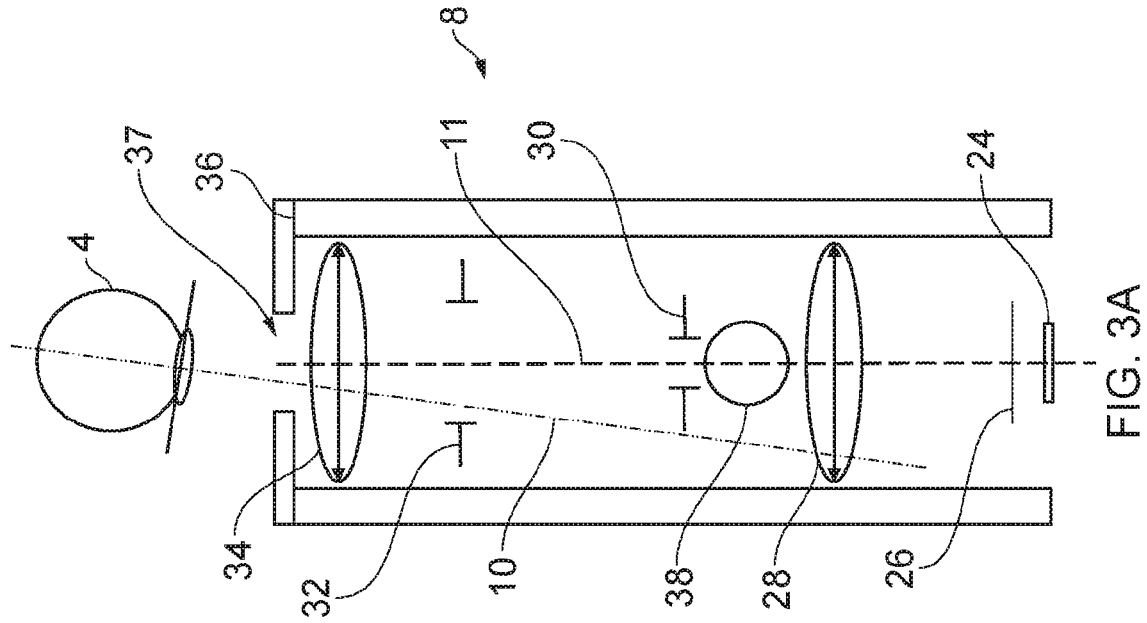
FIG. 3B is a schematic diagram of the optical elements contained within the imaging module with the first and second optical axes aligned.

FIG. 3A shows schematically the optical elements contained within the imaging module 8 of FIG. 1A and FIG. 2 prior to alignment of the first 10 and second 11 optical axes, with FIG. 3B showing the optical elements contained within the imaging module 8 with the first 10 and second 11 optical axes aligned. More specifically, the imaging module 8 comprises a housing 36 which encloses the optical elements including a sensor 24, a filter 26, camera optics 28, aperture stop 30, field stop 32, objective optics 34 and light source 38. As explained further below the orientation and position of the imaging module 8 can be adjusted to effect alignment of the second optical axis 11 with the first optical axis 10. The Applicant has recognised that the entrance pupil 37 of the imaging module 8 should align with the pupil of the eye 4 to provide good image quality. If the entrance pupil 37 is positioned incorrectly relative to the eye's pupil, the eye's pupil may block light entering the eye and may also block parts of the back-reflected light from reaching the imaging module 8. Mis-alignment may also cause the light directly reflected from the edge of the pupil to be back-scattered directly into the imaging module 8. This stray light will negatively impact the signal to noise ratio of the captured images. As such, it is important that the entrance pupil 37 of the imaging module 8 is properly aligned to the eye's physical pupil.

The alignment between the first optical axis of the eye 10 and the second optical axis of the imaging module 11 is shown in FIG. 3B.

Figure 12:
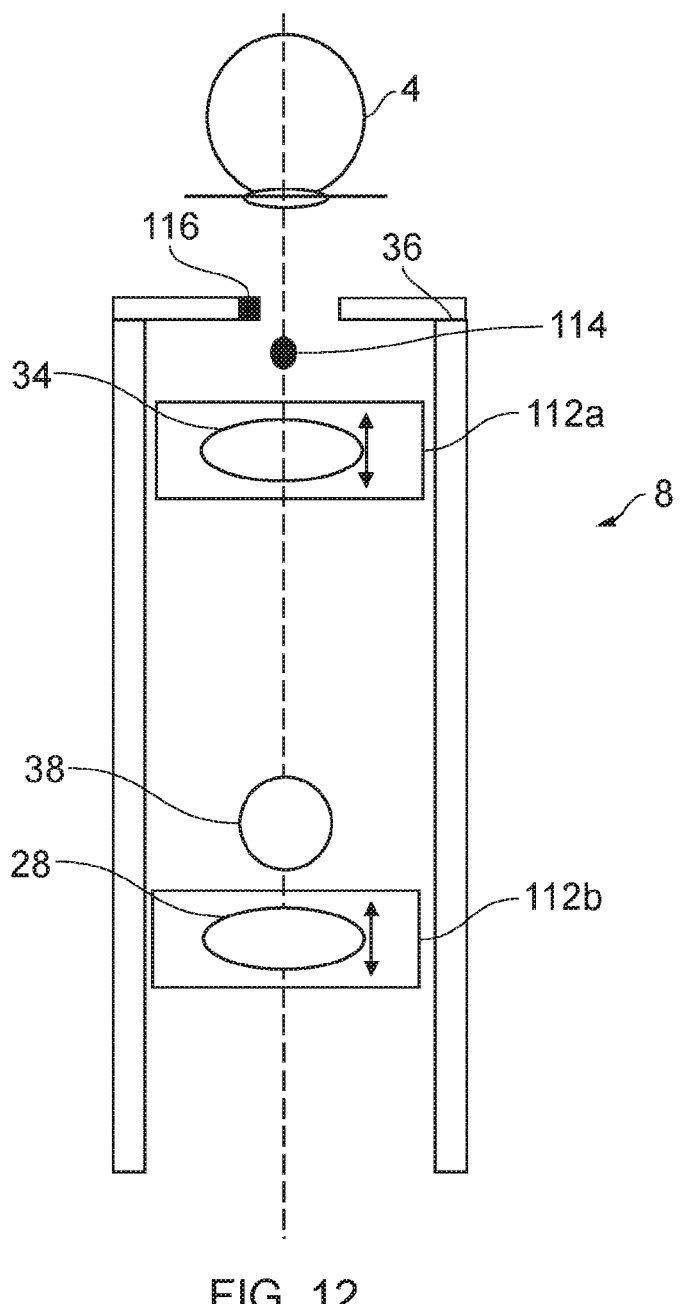
FIG. 12 is a simplified schematic diagram of the imaging module of FIGS. 3A and 3B, including focusing motors and a reticle.

FIG. 12 shows a simplified schematic of the imaging module 8, and includes a focusing mechanism comprising two focusing motors 112a, 112b. These focusing motors are arranged to move the optical elements 28, 34 towards or away from the eye 4 to focus the image of the retina. It is not essential that two motors are provided; one may be sufficient. The imaging module 8 also includes a reticle 114. The reticle 114 is visible to the patient and provides a fixation target for the patient to look at, to make sure the eye 4 is kept relatively still during alignment and image capture. An external light source 116 may illuminate the reticle making it visible for the patient during alignment, but briefly shutting off while capturing the RGB image to improve image quality.

The motors 20 A, B, C, A', B', C' in FIG. 2 are for movement of the imaging module 8 in order to align the first optical axis 10 of the patient's eye 4 with the second optical axis 11 of the imaging module 8. The motors 20 A, B, C, A', B', C' are connected and fixed to the support structure 22. The support structure 22 ensures the motors 20 A, B, C, A', B', C' retain a fixed position as the imaging module 8 is moved relative to the motor positions. The motors 20 A, B, C, A', B', C' move the imaging module 8 via the connections 21.

The imaging module 8 can be moved in any of five degrees of freedom—the X (16), Y (14), Z (12) directions, as well as tilt 18 in two directions. The sixth degree of freedom, roll, is not critical in this embodiment of the invention but could also be implemented in an alternative embodiment through use of additional motors. For example, to move in the Y direction, motors 20A, 20A' pull the imaging module 8 equally via the connections 21, whilst motors 20B, 20B' 20C, 20C' release force by increasing the length of the connections 21 to move the imaging module 8 upwards.

Figure 4:
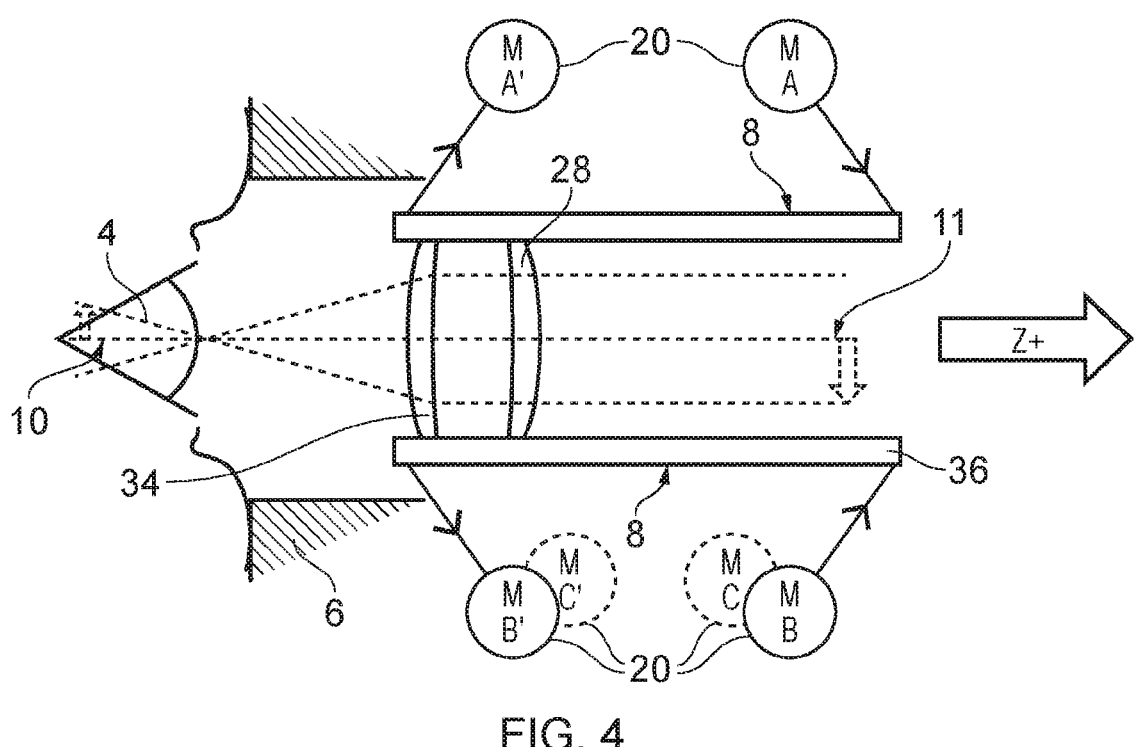
FIG. 4 is a schematic cross-sectional view of the imaging device of FIG. 1A using the motor configuration of FIG. 2.
Figure 5:
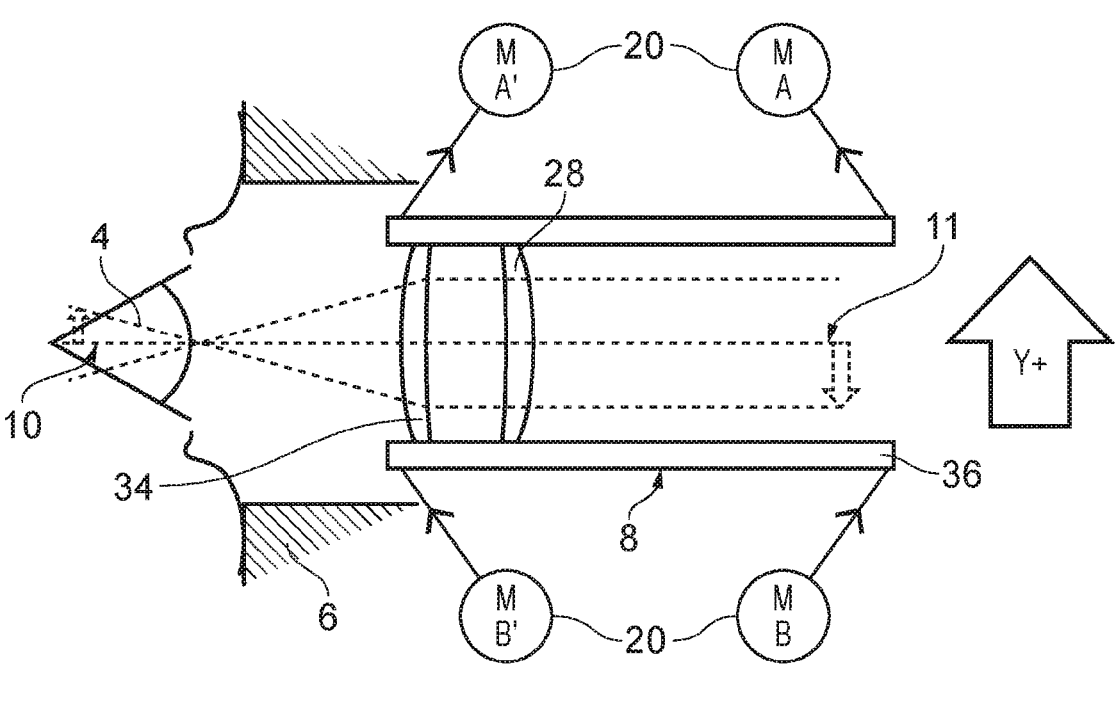
FIG. 5 is a view similar to FIG. 4 showing adjustment in a different direction.

FIG. 4 and FIG. 5 show schematic cross-sectional views of the imaging device of FIG. 1A using the motor configuration shown in FIG. 2 and the internal optics shown in FIGS. 3A and 3B. The eye rest 6 rests against the orbital of the patient's skull, which surrounds the patient's eye 4 to be imaged. The eye rest 6 is connected to the external housing 36 of the imaging device 2 to enable the patient to rest against the eye rest 6, providing a fixed position for imaging to occur. As in FIG. 1A, the first optical axis 10 of the patient's eye 4 is aligned with the second optical axis 11 of the imaging module 8. The additional dashed lines indicate paths of light through the imaging module 8 and eye 4. The motors 20 A, B, C, A', B', C' are each able to pull the imaging module 8 to allow for a five-axis movement in order to align the second optical axis 11 of the imaging module 8 and associated internal optics with the first optical axis 10 of the patient's eye 4, and to ensure the entrance pupil of the imaging module 8 is aligned with the physical pupil of the eye 4.

Figure 10A:
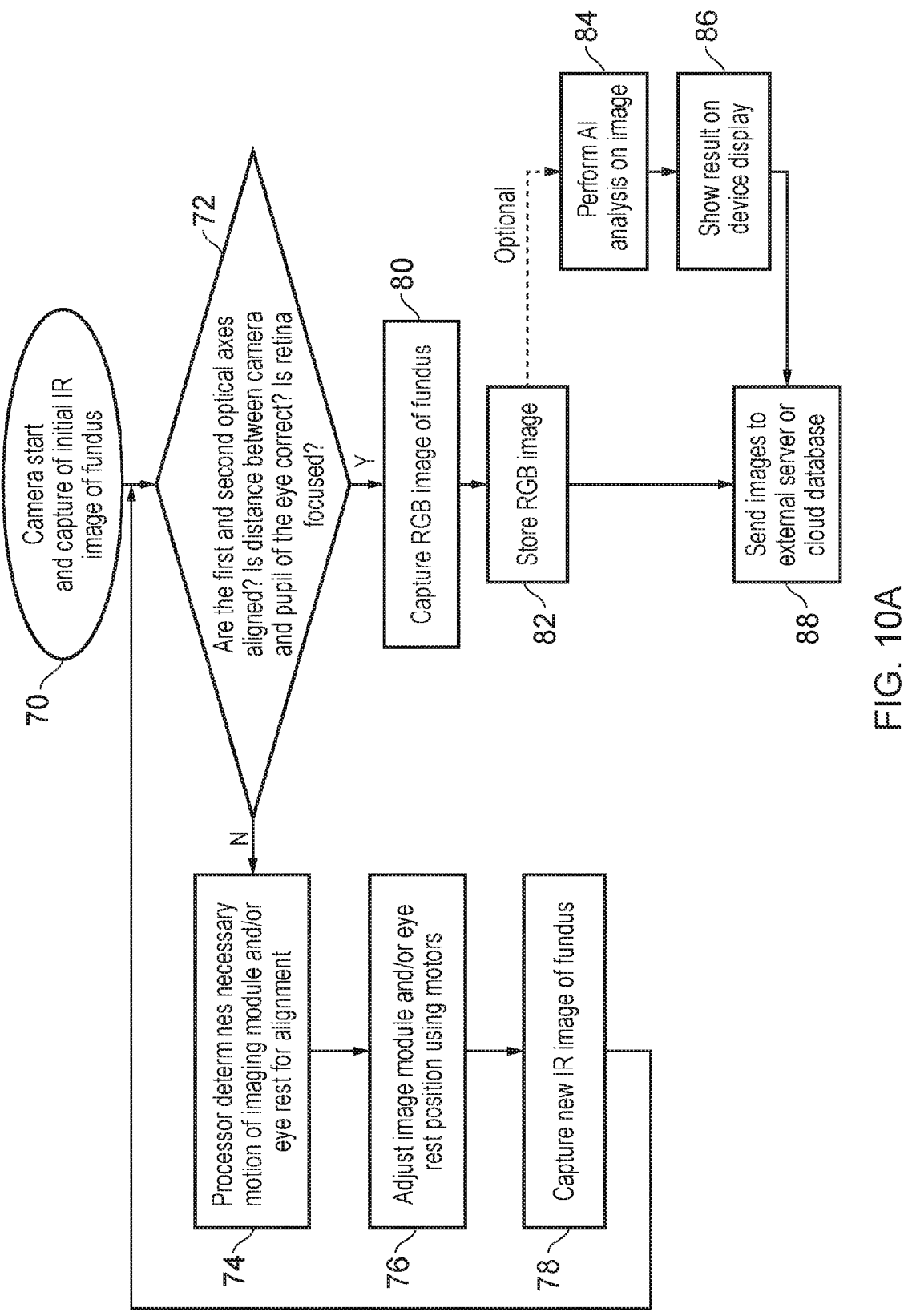
FIG. 10A is a flowchart illustrating a method of using the imaging device.

To capture an optimised image where the first 10 and second 11 optical axes are aligned and the image is focused, adjustments of the position of the imaging module 8 occur in response to the feedback control system as shown in FIG. 10A. In step 70, an initial image is captured in IR using the imaging device 2. In order to optimise the image, in step 72 the processor 60 then analyses the image to identify whether the first 10 and second 11 optical axes are aligned, and whether the entrance pupil 37 of the imaging module 8 is aligned with the physical pupil of the eye 4. If they are not aligned, in step 74 the processor 60 determines the necessary motion of the imaging module 8 and/or eye rest 6 for alignment of the first 10 and second 11 optical axes. In step 76, the required adjustments are made to the position of the imaging module 8 using the motors 20. In step 78, a new image is captured in IR by the imaging device 2, with this new image again analysed by the processor 60 in step 72 to identify if further adjustments are necessary. If further adjustments are necessary, steps 74-78 are repeated until the first 10 and second 11 optical axes are aligned and the image is in focus.

A final high resolution RBG image is then captured in step 80. Next, in step 82, this RGB image is stored in the memory 62. Optionally, the processor 60 then performs AI analysis on the image in step 84, displaying the result on the device display screen 13 in step 86. When the images are ready to be sent to an external server 66, in step 88 the imaging device 2 is connected using either a wired connection or wirelessly to the base unit 64 and the base unit 64 then sends the stored RBG images to the external server 66 or a cloud database for further processing or storage.

The Applicant has recognised that aspects of the image when the imaging module 8 entrance pupil is imperfectly aligned to the eye's physical pupil can be used to make fine adjustments to the positioning, using a model which could dictate necessary adjustments based on the nature of the image features. For this procedure to work, a database correlating known mis-alignments to real image features can be used. The applicant has also recognised that in order for this approach to work, the initial alignment should be close to perfect (within 1-2 mm), and often this is difficult to achieve with untrained operators.

FIG. 4 shows how movement of the imaging module 8 in the Z direction can be achieved. This would be necessary if the distance between the eye and the imaging module 8 needed to be altered. Motors 20 A', B', C' are pulling the imaging module 8 whilst motors 20 A, B, C are releasing force by increasing the length of the connections 21. This has a net result of moving the imaging module 8 away from the patient's eye 4 in the Z+ direction.

FIG. 5 shows how movement in the Y direction can be achieved using the motor configuration as shown in FIG. 2. This would be necessary if the imaging device 2 is positioned incorrectly relative to the patient's eye 4 such that the respective optical axes are parallel but offset. Motors 20 A and A' are pulling the imaging module 8 whilst motors 20 B, B', C, C' are releasing force by increasing the length of the connections 21. This has a net result of moving the imaging module 8 vertically upwards in the Y+ direction.

The imaging device 2 as shown in FIG. 1A is portable and battery powered and can thus either be brought towards the patient's eye 4 by a person who is performing the imaging or by the patient themselves. Alternatively the imaging device 2 could be fixed on a horizontal surface such as a table, or mounted on a wall or ceiling, with the patient moving themselves towards the fixed imaging device 2. The patient or person carrying out the imaging moves the imaging device 2 or themselves such that the eye rest 6 of the imaging device is in contact with the orbital of the patient's skull which surrounds the eye socket. The motors 20 then automatically align the imaging module using a feedback control system in order that the patient's eye 4 is aligned with the imaging module 8 along the first 10 and second 11 optical axes.

In order to produce an image of the fundus of the eye, a light source 38 emits a pulse of light which passes through the optical elements 30, 32, 34 as shown in FIGS. 3A and 3B. The light is reflected from the fundus of the patient's eye 4, and returns through the imaging module 8 and the optical elements 34, 32, 30, 28, 26 to produce an image on the sensor 24 which can be stored on a removable storage device for later analysis.

The light source is a circular ring light source centred on the second optical axis 11, circumscribing (or in close proximity) to the aperture stop 30. The ring light source may be arranged as a ring of alternating IR light and visible white light LEDs. In one mode the visible white light LEDs may be used to illuminate the eye, in another mode the IR LEDs may be used to illuminate the eye.

The camera optics 28 may be an achromatic lens. The aperture stop 30 is an opening which limits the amount of light which passes through the imaging module 8. The amount of light which passes through the imaging module 8 needs to be limited and controlled by the aperture stop 30. This is in order that enough light is reflected from the fundus of the eye 4 that the sensor 24 can detect the reflected light to form an image, but not too much light is incident on the fundus of the eye 4 such that the sensor 24 is overexposed. There needs to be a high enough light intensity such that there is a high signal to noise ratio on the captured image on the sensor 24.

The focused light then passes through the field stop 32. The field stop 32 limits the size/angular breadth of the object (the fundus of the eye 4) which is being imaged by the imaging module 8. The width of the field stop 32 is set such that the entirety of the fundus of the eye is imaged by the imaging module 8.

The light then passes through the objective optics 34 which could comprise one or more lenses. The lens(es) may be achromatic. The objective optics 34 focus the incident light such that the light focuses on the fundus of the patient's eye 4, where only 2-5% may be reflected (depending on wavelength). The reflected light then passes back through the objective optics 34, the field stop 32, the aperture stop 30, the camera optics 28, optionally the filter 26 which is used to filter out any wavelengths of the incident light pulse which are not desired to be used for the imaging and onto the sensor 24 where the reflected light is detected and used to produce an image of the fundus of the patient's eye 4.

Figures 6A, 6B:
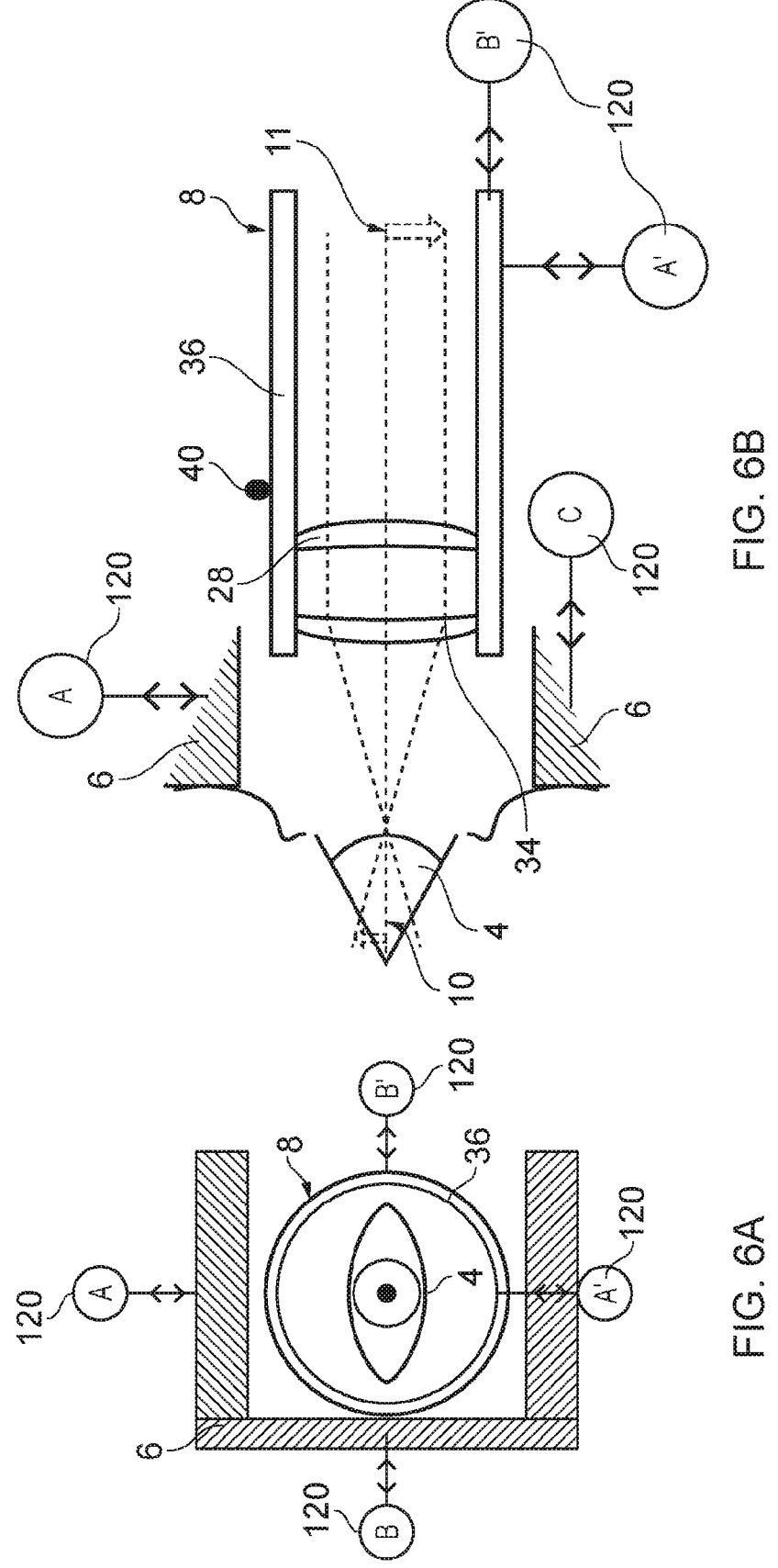
FIG. 6A is a front view of an embodiment of an imaging device which includes a motor controlled eye rest.
FIG. 6B is a cross-sectional view of the imaging device of FIG. 6A.

FIG. 6A and FIG. 6B show a further embodiment of the current invention, where three motors 120 A, B, C are arranged to translate the eye rest 6 in the XYZ direction relative to the imaging module 8.

FIG. 6A is the front view of this alternative embodiment and FIG. 6B is a cross-sectional view of the imaging device as shown in FIG. 6A. The eye rest 6 surrounds three sides of the imaging module 8. The patient/clinician places the imaging device comprising the eye rest 6, the imaging module 8 and the motors 120 A, B, C, A', B' against the orbital of a patient's skull which surrounds the eye socket. In this embodiment the eye rest 6 surrounds three sides of the imaging module 8, however the eye rest may also be constructed such that only one side contacts the patient e.g. the patient's forehead. In further embodiments it may be advantageous to block any external light when carrying out the imaging and the eye rest may prevent external stray light from entering the eye under study, or the other eye. Making sure the eye is kept under as dark conditions as possible will make sure the pupils are fully dilated during the imaging procedure. Blocking any external light with the eye rest can prevent unwanted stray light from entering the imaging module 8, thus improving image quality.

Some of the motors 120 A, B, C provide movement of the eye rest 6 in the X, Y and Z directions. The imaging module 8 is fixed to a swivel point 40 about which the imaging module 8 can be rotated by motors 120 A' and B'. The position of the swivel point 40 can be selected to be any point along the length of the imaging module 8. If the swivel point 40 is selected to be at the midpoint of the length of the imaging module 8 this provides mechanical stability and motor movement span balance. The swivel point 40 could also be selected to be closer to the patient's eye 4 along the extent of the imaging module 8. The swivel point 40 could be selected to be at the same position along the imaging module 8 as the aperture stop is positioned internally along the imaging module 8.

The eye rest 6 is moved by its associated motors 120 A, B, C independently relative to the imaging module 8 which is moved by its associated motors 120 A', B'. Through a combination of the rotation of the imaging module 8 and adjustment of the position of the eye rest 6, the first optical axis 10 of the patient's eye 4 can be aligned with the second optical axis 11 of the imaging module 8. Independent movement of the eye rest 6 and the imaging module 8 may in some cases enable a wider range of relative motion between the imaging module 8 and patient's eye 4 than when motors 120 A, B, C, A', B' are only connected to the imaging module 8, as in the embodiment shown in FIG. 2.

Figure 7B:
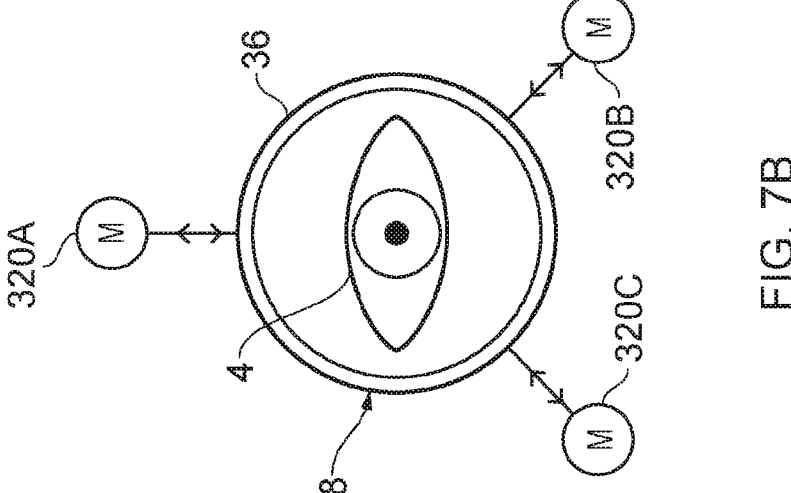
FIG. 7B is a schematic diagram of the motors and imaging module of another embodiment with a symmetric motor distribution.
Figure 7A:
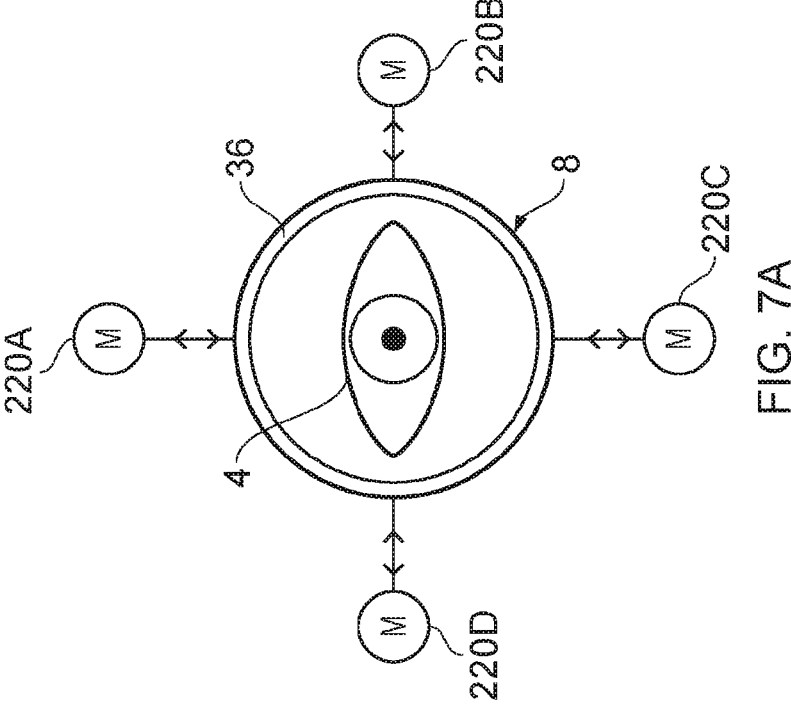
FIG. 7A is a schematic diagram of the motors and imaging module with a symmetric motor distribution.
Figure 7C:
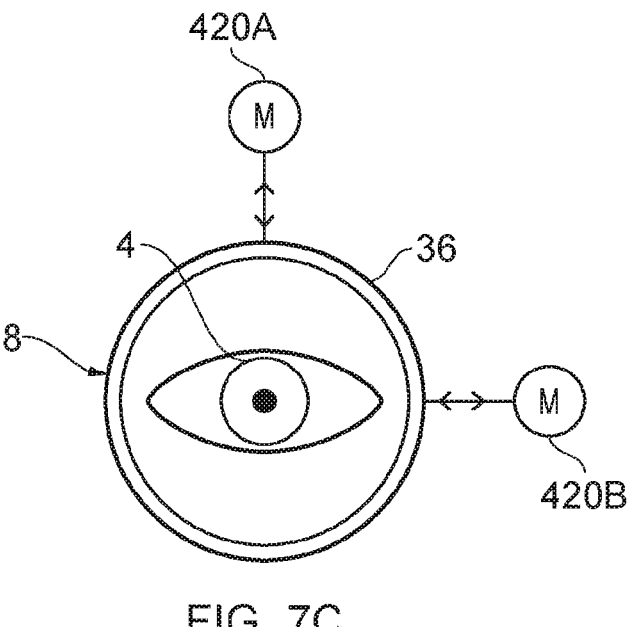
FIG. 7C is a schematic diagram of the motors and imaging module of another embodiment with an asymmetric motor distribution.

FIG. 7A, 7B, 7C show further embodiments of the external motor configuration surrounding the imaging module 8. For these configurations a separate motor would be needed for alignment along the Z-axis (towards/away from the eye 4).

FIG. 7A is a schematic diagram showing four motors 220 A, B, C, D which are arranged symmetrically around the imaging module 8, centred on the patient's eye 4. The motors 220 A, B, C, D act on the imaging module housing 36.

FIG. 7B is an alternative schematic diagram showing three motors 320 A, B, C which are arranged symmetrically around the imaging module 8, centred on the patient's eye 4 so as to act on the imaging module 8.

FIG. 7C is a schematic diagram showing two motors 420A, 420B which are distributed asymmetrically about the imaging module 8 which is centred on the patient's eye 4. The asymmetric distribution arises as the two motors 420A, 420B are at an angular separation of 90°. As the two motors are asymmetrically distributed, one of the motors 420A provides up and downwards movement of the imaging module 8 through pull or pushing it. The other motor 420B provides left and right movement through pushing or pulling the imaging module 8. Motion may therefore be achieved in any direction in the XY plane.

Increasing the number of motors 420 arranged to move the imaging module may result in a finer control of the imaging module 8, however two motors may provide enough motion of the imaging module 8 in some circumstances.

In FIG. 7A, 7B, 7C, the motors which are arranged to move the imaging module 8 either push or pull the imaging module 8 to align its associated second optical axis 11 with the first optical axis 10.

Figure 8A:
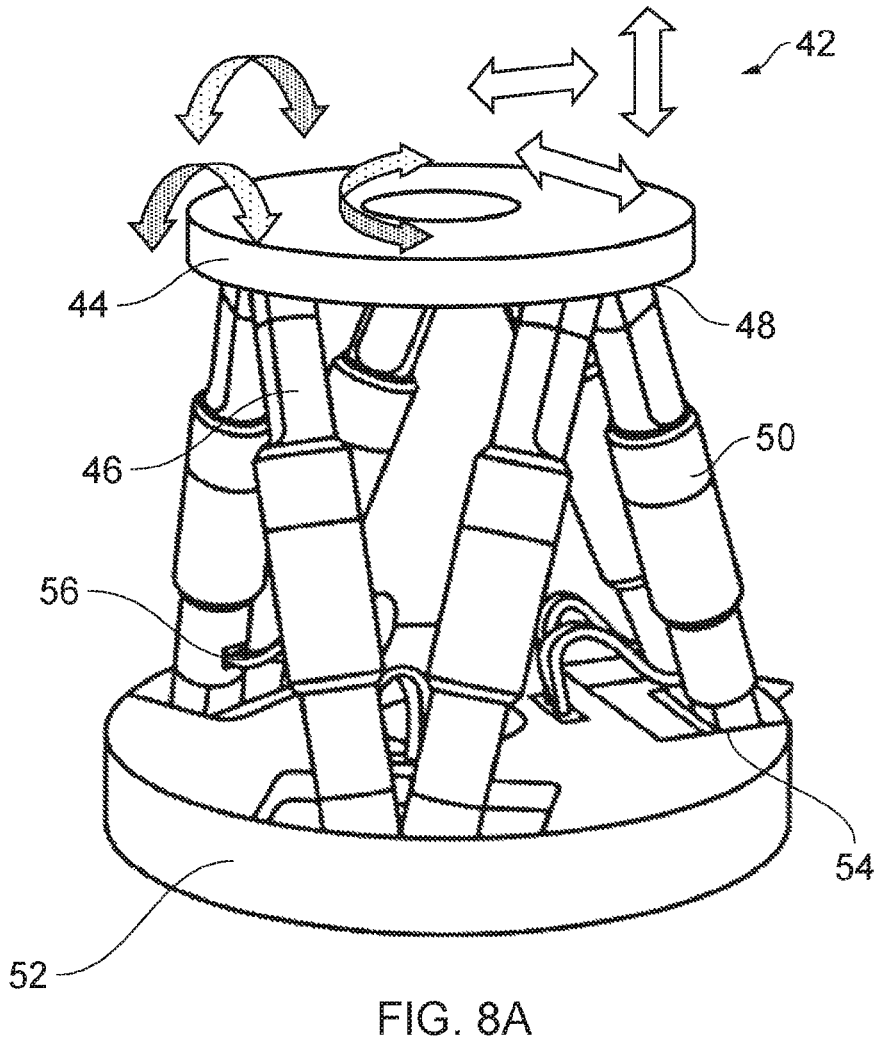
FIG. 8A shows a Stewart platform which can be used in embodiments of the invention.

FIG. 8A shows a Stewart platform 42 which is an alternative motor configuration to those displayed in FIG. 2 and FIGS. 7A-C for movement of the imaging module 8 containing the imaging optics. The Stewart platform 42 consists of a platform 44 which is connected to an end of each of six linear actuators 46 at the mounting points 48. The opposite end of the linear actuators 46 are connected to the baseplate 52 at the base connection points 54. Electrical connections 56 provide power to the motors 50 which drive the linear actuators 46.

Adjacent pairs of linear actuators 46 are attached in pairs to the baseplate 52 at the base connection points 54. The linear actuators 46 extend away from the base connections 54 and the baseplate 52 to the mounting points 48 on the platform 44, crossing over towards the other adjacent linear actuator 46, such that there are three mounting points 48. The length of the linear actuators 46 are adjusted by six motors 50.

Figure 8C:
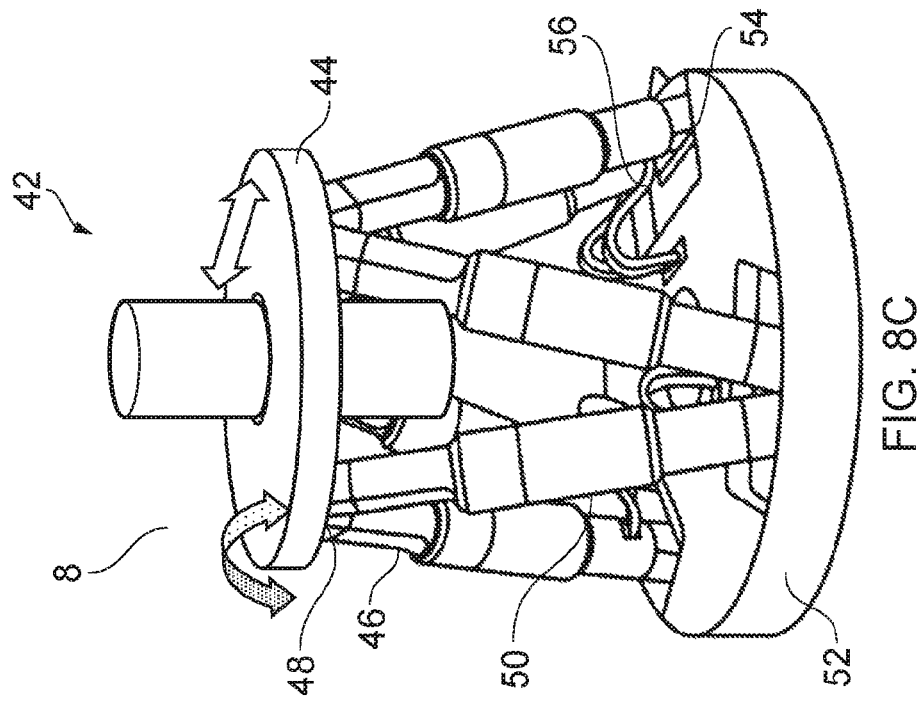
FIG. 8C shows the imaging module of another embodiment fixed vertically through the geometric centre of a Stewart platform, perpendicular to the platform.
Figure 8B:
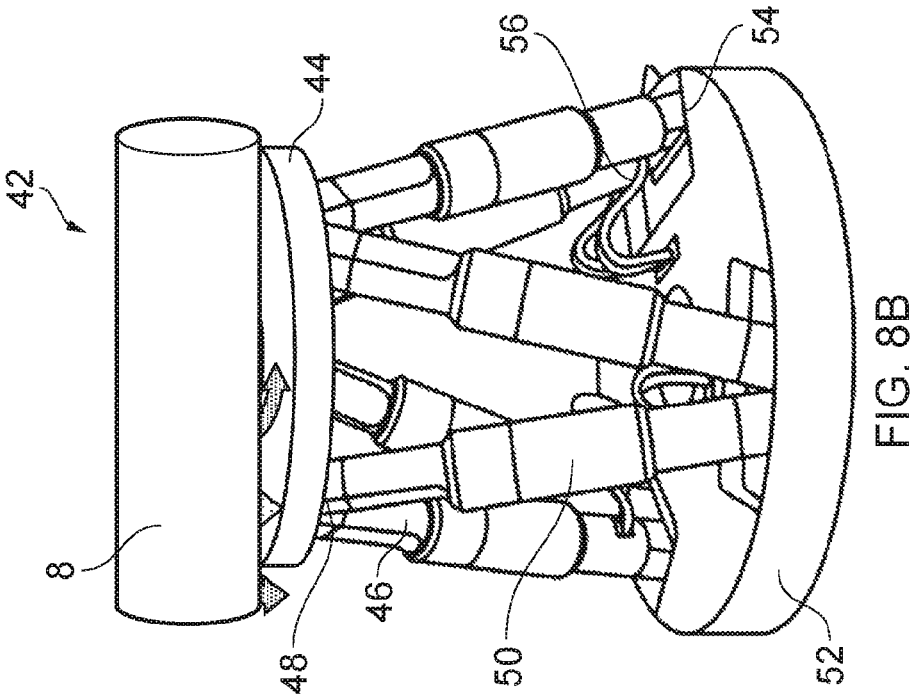
FIG. 8B shows the imaging module of another embodiment of the invention fixed horizontally onto a Stewart platform.

FIG. 8B shows the imaging module 8 fixed horizontally to and parallel to the platform 44 of the Stewart platform 42 in FIG. 8A. FIG. 8C shows the imaging module 8 fixed vertically through and perpendicular to the geometric centre of the platform 44 of the Stewart platform 42 in FIG. 8A.

As the length of the linear actuators 46 can each be individually driven by a motor 50 and the base connections 54 are configured to allow the linear actuators 46 to be adjusted in any direction, the position of the platform 44 can be adjusted in six possible degrees of freedom (X, Y, Z, roll, tilt in two directions). The imaging module 8 which is either fixed horizontally (FIG. 8B) or vertically (FIG. 8C) to the platform 44 can therefore be aligned along the optical axis 10 for imaging of the fundus of the eye.

As an example, in order to move the platform 44 to which the imaging module 8 is fixed up and down with respect to the base 52 of the Stewart platform, the motors 50 drive the linear actuators 46 such that they either extend or shorten together as appropriate to give motion up or down. For this motion, all six linear actuators 46 must be the same length in order that the horizontal platform 44 remains horizontal. Alternatively, if the platform 44 was required to tilt in order to align the first and second optical axes, the motors 50 would drive the linear actuators 46 by different amounts in order that the linear actuators 46 connected to one side of the platform 50 were longer than the linear actuators connected to the other side of the platform 50. This would have a net result of the platform 50 tilting.

Figure 9:
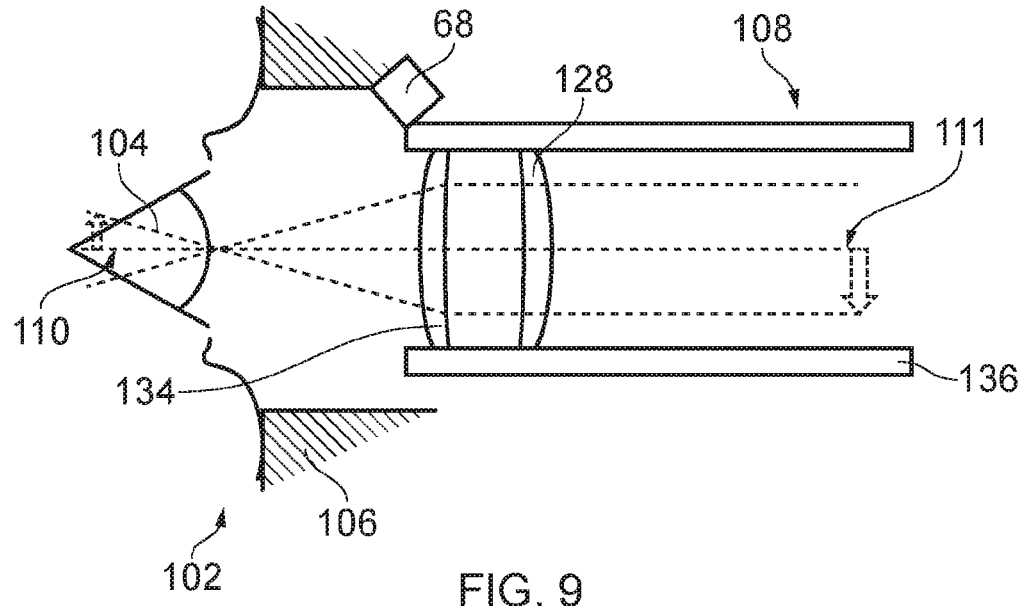
FIG. 9 is a cross sectional view of an embodiment of an imaging device which includes an external camera.

FIG. 9 shows a further embodiment of the imaging device 102, where an external camera 68 is connected to the outer housing 136 of the imaging module 108. The external camera 68 is used to detect the location and gaze direction of the patient's pupil which will therefore enable the processor 60 to determine the direction of the first optical axis 110. Motors are then used to move the imaging module 108 such that its associated second optical axis 111 is aligned with the first optical axis 110 and the main camera contained within the imaging module 108 can be used to capture an image. The external camera 68 may be located freely anywhere around the imaging module 108. The external camera 68 has a separate light source to the imaging module 108 and therefore the external camera 68 and imaging module 108 may emit light at two different wavelengths for alignment and imaging respectively.

Figure 11:
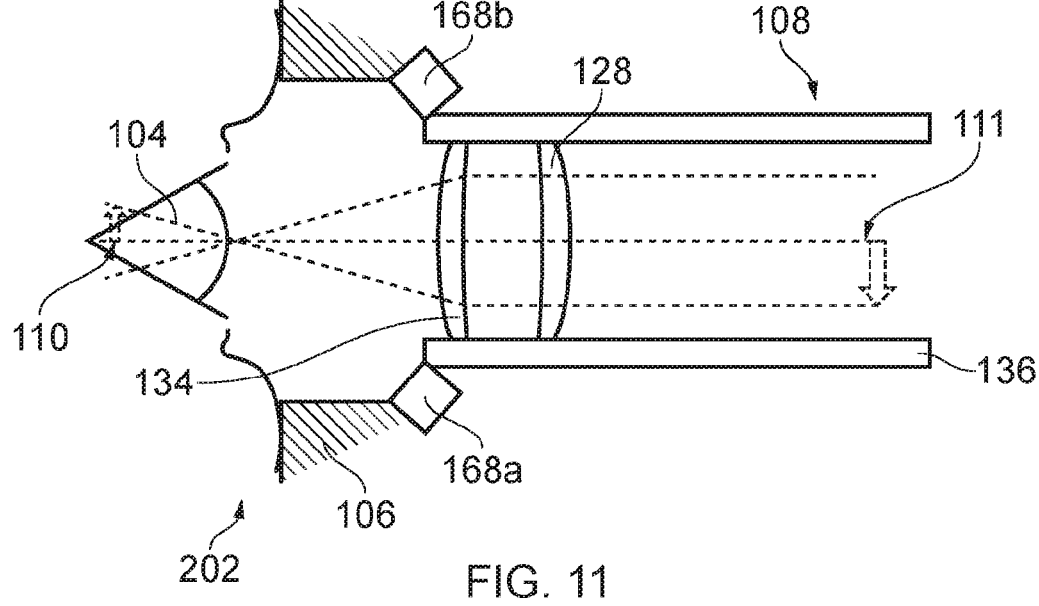
FIG. 11 is a cross sectional view of an embodiment of an imaging device which includes two external cameras.

FIG. 11 shows a further embodiment of the imaging device 202 similar to the imaging device 102 shown in FIG. 9, however there are two separate external cameras 168a and 168b connected to the outer housing 136 of the imaging module 108. In such a case a more accurate 3D positioning of the pupil relative to the imaging module 8 can be calculated through use of stereo imaging.

Figure 10B:
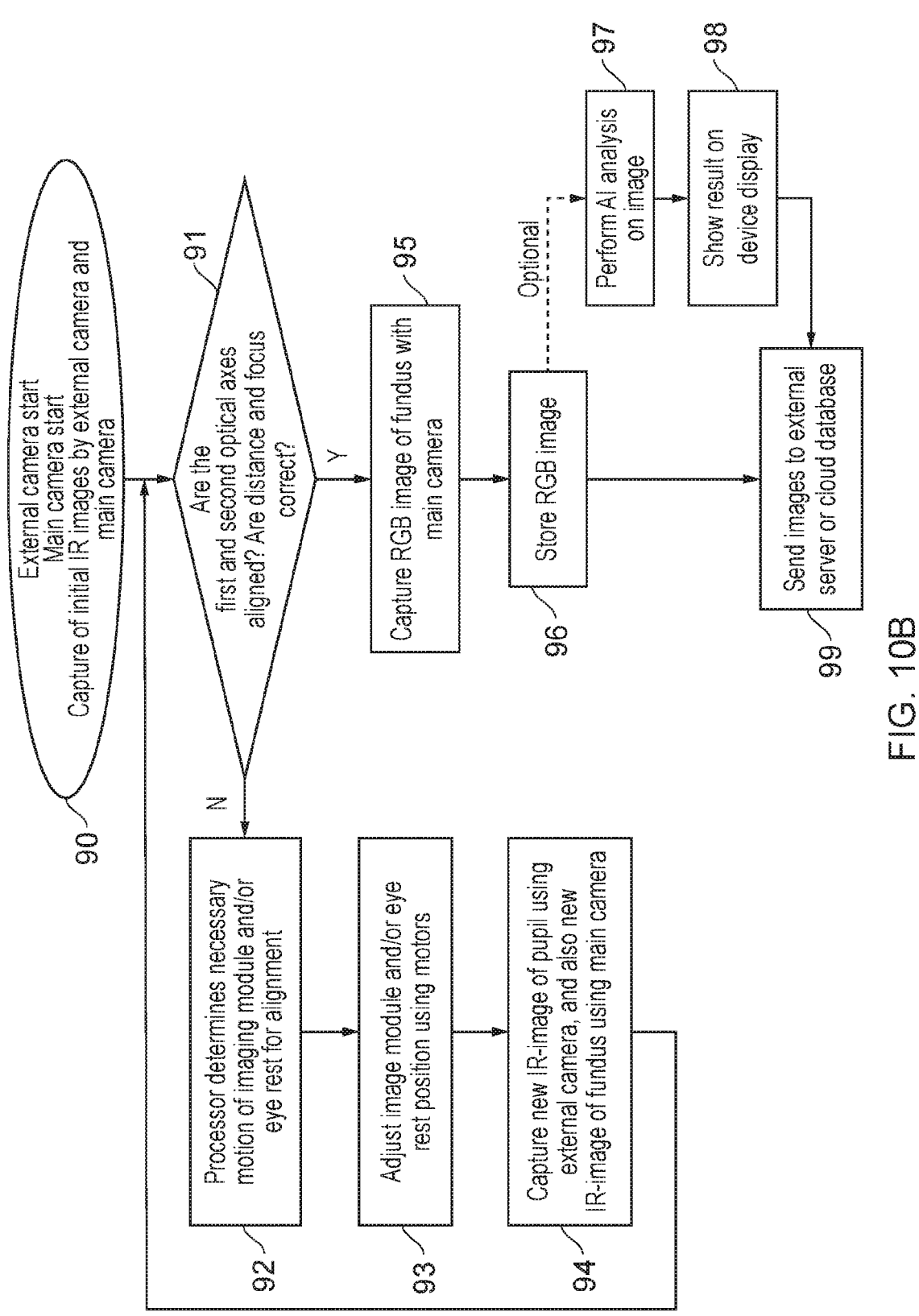
FIG. 10B is a flowchart illustrating a method of using the imaging device which includes an external camera.

To capture an optimised image where the first 110 and second 111 optical axes are aligned and the image is focused, adjustments of the position of the imaging module 108 occur in response to the feedback control system as shown in FIG. 10B. In step 90, the external camera 68, 168a, 168b and main camera start. An initial image is captured using the main fundus camera and external camera 68, 168a, 168b, both under IR illumination. In order to optimise the image, in step 91 the processor then analyses the images to identify whether the first 110 and second 111 optical axes are aligned, as well as making sure the entrance pupil 37 of the imaging module 8 is aligned with the physical pupil of the eye. If they are not aligned, in step 92 the processor determines the necessary motion of the imaging module 108 and/or eye rest 106 for alignment of the first 110 and second 111 optical axes, and the entrance pupil and eye pupil. In step 93, the required adjustments are made to the position of the imaging module 108 and eye rest 106 using the motors. In step 94, new images are captured by the main fundus camera and the external camera 68, 168a, 168b, with these new images again analysed by the processor in step 91 to identify if further adjustments are necessary. If further adjustments are necessary, steps 92-94 are repeated until the first 110 and second 111 optical axes are aligned, the entrance pupil 37 is aligned and the image is in focus.

In general the external camera is used for providing alignment information on a coarse scale, while the internal fundus camera can provide alignment information for fine-grained alignment.

A final high resolution RBG image is then captured in step 95 using the main camera provided by the imaging module 108. Next, in step 96, this RGB image is stored in the memory. Optionally, the processor then performs AI analysis on the image in step 97, displaying the result on the device display screen 13 in step 98. When the images are ready to be sent to an external server, in step 99 the imaging device 102 is connected using either a wired connection or wirelessly to the base unit and the base unit then sends the stored RBG images to the external server or a cloud database for further processing or storage. Alternatively the processor can be connected directly to the external server or cloud database.

It will be appreciated by those skilled in the art that the invention has been illustrated by describing one or more specific embodiments thereof, but is not limited to these embodiments; many variations and modifications are possible, within the scope of the accompanying claims. For example it is envisaged that the imaging device may be large enough and the motors have a long enough operating/travel length that both eyes of the patient can be imaged without the need to reposition the device for each eye.

The invention claimed is:

1. An ophthalmic imaging device suitable for imaging the fundus of an eye, the imaging device comprising:
  (a) one or more light sources arranged to illuminate the fundus at at least two different wavelengths;
  (b) an imaging system comprising imaging optics and an image sensor, wherein the imaging optics include multiple lenses forming an achromatic lens configuration;
  (c) an alignment system including a plurality of motors, wherein one or more motors of the plurality of motors are arranged to move an eye rest of the imaging device and one or more other motors of the plurality of motors are arranged to move an imaging module of the imaging device independently from the eye rest, such that the eye rest is movable in XYZ directions and the imaging module orientation is independently controllable in pan and tilt directions; and (d) a focussing system;

wherein the imaging device is arranged to illuminate the fundus using the one or more light sources at a first wavelength while aligning an optical axis of the imaging system with an optical axis of the eye, using the alignment system, wherein the imaging device is also arranged to illuminate the fundus using the one or more light sources at the first wavelength during focussing using the focussing system, wherein the imaging device is also arranged to illuminate the fundus using the one or more light sources at a second wavelength while imaging the fundus onto the image sensor using the imaging system;

wherein light at the first wavelength is infrared light, and light at the second wavelength is visible light;

wherein the achromatic lens configuration is configured so that a focal length of the achromatic lens configuration using infrared light at the first wavelength is also the focal length for an image taken by the imaging system using visible light at the second wavelength;

wherein the imaging module is fixed to a swivel point about which the imaging module is rotated by the plurality of motors of the alignment system, and wherein the plurality of motors are symmetrically arranged around an optical axis of the imaging module;

wherein the motors are controlled by a feedback control system which comprises a processor that processes data in accordance with an algorithm based on machine learning; and wherein the processor is programmed to perform an artificial intelligence algorithm that analyzes captured images and generates and displays information on the imaging device regarding whether a further referral is to be sought based on the analysis of the captured images.

2. The ophthalmic imaging device of claim 1, wherein the achromatic lens configuration includes at least one achromatic lens.

3. The ophthalmic imaging device of claim 1, wherein a first light source is used to illuminate the eye at the first wavelength and a second light source is used to illuminate the eye at the second wavelength.

4. The ophthalmic imaging device of claim 1, wherein the imaging device further includes a first alignment camera mounted on an exterior portion of the imaging device, wherein the first alignment camera images the eye using light at the first wavelength, and wherein resultant images are used by the alignment system to align an optical axis of the imaging system with an optical axis of the eye.

5. The ophthalmic imaging device of claim 4, wherein the first alignment camera has a separate light source which emits light at the first wavelength and also at a third wavelength, which is also infrared light.

6. The ophthalmic imaging device of claim 4, wherein a second alignment camera is mounted on an exterior portion of the imaging device.

7. The ophthalmic imaging device of claim 6, wherein the first and second alignment cameras are used for stereo imaging.

8. The ophthalmic imaging device of claim 4, wherein the first alignment camera is adapted to detect a location and gaze direction of the eye.

9. The ophthalmic imaging device of claim 4, wherein the first alignment camera mounted on the exterior portion of the imaging device provides alignment information at a first scale, and a fundus camera included in the imaging device provides alignment information on a second scale, finer than the first scale.

10. The ophthalmic device of claim 1, wherein the visible light is white light.

11. The ophthalmic device of claim 1, wherein the visible light is red, green, and blue light.

12. The ophthalmic device of claim 1, wherein the visible light is of a combination of wavelengths.

13. The ophthalmic device of claim 1, wherein the device is configured to capture a plurality of narrow wavelength images.

14. The ophthalmic device of claim 13, wherein the plurality of narrow wavelength images, include a plurality of infrared and visible wavelength images.

15. The ophthalmic device of claim 1, wherein motors are used to align the optical axis of the imaging system with the optical axis of the eye, using the alignment system.

16. The ophthalmic device of claim 1, wherein motors are used to focus the imaging system with respect to the fundus, using the focussing system.

* * * * *